United States Patent [19]

Lau et al.

[11] Patent Number: 5,510,368

[45] Date of Patent: Apr. 23, 1996

[54] N-BENZYL-3-INDOLEACETIC ACIDS AS ANTIINFLAMMATORY DRUGS

[75] Inventors: Cheuk K. Lau, Ile Bizard; Cameron Black, Pointe Claire; Michel Belley, Pierrefonds, all of Canada

[73] Assignee: Merck Frosst Canada, Inc., Kirkland, Canada

[21] Appl. No.: 445,625

[22] Filed: May 22, 1995

[51] Int. Cl.⁶ .................. A61K 31/405; C07D 209/22
[52] U.S. Cl. ............................. 514/419; 548/494
[58] Field of Search ............................. 548/494; 514/419

[56] References Cited

U.S. PATENT DOCUMENTS

| | | |
|---|---|---|
| 3,161,654 | 12/1964 | Shen . |
| 3,196,162 | 7/1965 | Sarett et al. . |
| 3,242,163 | 3/1966 | Sarett et al. . |
| 3,242,193 | 3/1966 | Sarrett et al. ............................. 548/494 |
| 3,654,349 | 4/1972 | Shen et al. . |
| 3,725,548 | 4/1973 | Shen et al. . |

FOREIGN PATENT DOCUMENTS

| | | |
|---|---|---|
| 709843 | 5/1965 | Canada . |
| 709844 | 5/1965 | Canada ................................. 548/494 |
| 948460 | 2/1964 | United Kingdom .................. 548/494 |
| 957990 | 5/1964 | United Kingdom .................. 548/494 |
| 2225012 | 5/1990 | United Kingdom . |
| WO94/06769 | 3/1994 | WIPO . |

OTHER PUBLICATIONS

Chem. Abstracts, vol. 61, p. 4320(a) (1964) "Resolution of Substituted Indoles" 1-p-chlorobenzyl-2-methyl-5-methoxy-3-indolyl)propionic acid.

*Primary Examiner*—Patricia L. Morris
*Attorney, Agent, or Firm*—Curtis C. Panzer; David L. Rose

[57] ABSTRACT

The invention encompasses the novel compound of Formula I as well as a method of treating inflammation and, in particular, cyclooxygenase-2 mediated diseases comprising administration to a patient in need of such treatment of a non-toxic therapeutically effective amount of a compound of Formula I.

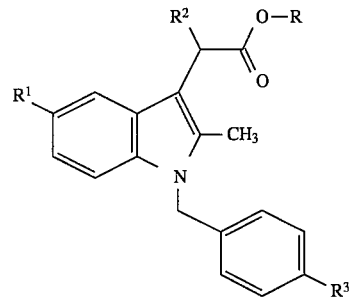

The invention also encompasses certain pharmaceutical compositions for treatment of inflammation and, in particular, cyclooxygenase-2 mediated diseases comprising compounds of Formula I.

9 Claims, No Drawings

N-BENZYL-3-INDOLEACETIC ACIDS AS ANTIINFLAMMATORY DRUGS

BACKGROUND OF THE INVENTION

This invention relates to methods of treating cyclooxygenase mediated diseases and certain pharmaceutical compositions therefor.

Non-steroidal, antiinflammatory drugs exert most of their antiinflammatory, analgesic and antipyretic activity and inhibit hormone-induced uterine contractions and certain types of cancer growth through inhibition of prostaglandin G/H synthase, also known as cyclooxygenase. Initially, only one form of cyclooxygenase was known, this corresponding to cyclooxygenase-1 or the constitutive enzyme, as originally identified in bovine seminal vesicles. More recently the gene for a second inducible form of cyclooxygenase (cyclooxygenase-2) has been cloned, sequenced and characterized initially from chicken, murine and human sources. This enzyme is distinct from the cyclooxygenase-1 which has been cloned, sequenced and characterized from various sources including the sheep, the mouse and man. The second form of cyclooxygenase, cyclooxygenase-2, is rapidly and readily inducible by a number of agents including mitogens, endotoxin, hormones, cytokines and growth factors. As prostaglandins have both physiological and pathological roles, we have concluded that the constitutive enzyme, cyclooxygenase-1, is responsible, in large part, for endogenous basal release of prostaglandins and hence is important in their physiological functions such as the maintenance of gastrointestinal integrity and renal blood flow. In contrast, we have concluded that the inducible form, cyclooxygenase-2, is mainly responsible for the pathological effects of prostaglandins where rapid induction of the enzyme would occur in response to such agents as inflammatory agents, hormones, growth factors, and cytokines. Thus, a selective inhibitor of cyclooxygenase-2 will have similar antiinflammatory, antipyretic and analgesic properties to a conventional non-steroidal antiinflammatory drug, and in addition would inhibit hormone-induced uterine contractions and have potential anti-cancer effects, but will have a diminished ability to induce some of the mechanism-based side effects. In particular, such a compound should have a reduced potential for gastrointestinal toxicity, a reduced potential for renal side effects, a reduced effect on bleeding times and possibly a lessened ability to induce asthma attacks in aspirin-sensitive asthmatic subjects.

Such a compound would also be of use in the treatment of Alzheimer's disease and osteoporosis.

A brief description of the potential utility of cyclooxygenase-2 is given in an article by John Vane, *Nature*, Vol. 367, pp. 215–216, 1994.

U.S. Pat. No. 3,196,162 (Jul. 20, 1965) discloses structures of anti-inflammatory agents which differ from the present compounds most notably by the presence of the 5-methoxy substituent which we have shown to be inferior to the 5-halo analogs of the present invention. WO 93/00334 discloses structures which differ from the present compounds in being 3-indoleacetamides and having no substitution at the 2- and 5-positions. Khim Geterotsikl, Soedin., (1), 100-2, 1969 discloses structures which differ from the present compounds notably by being 3-indolecarboxylic acid. UK patent application 2,225,012 (May 23, 1990) discloses a series of indole-2 (or -3)-alkanoic acid as being anti-thrombotic agents, but which differ from the present compounds by having no substituent on the 1-benzyl group and by having at least 4-carbon atoms in the 2-substituent. Merck Frosst has a series of patents disclosing N-benzylindole alkanoic acids (U.S. Pat. Nos. 5,081,145, 5,202,321 and 5,204,344). However, these differ structurally from the present compounds in that they carry the alkanoic acid in the 2-position rather than the 3-position. The compounds of these Merck Frosst patents are of use as prostaglandin antagonists, inhibitors of leukotriene biosynthesis or as synthetic intermediates.

SUMMARY OF THE INVENTION

The invention encompasses the novel compound of Formula I as well as a method of treating inflammation and, in particular, cyclooxygenase-2 mediated diseases comprising administration to a patient in need of such treatment of a non-toxic therapeutically effective amount of a compound of Formula I.

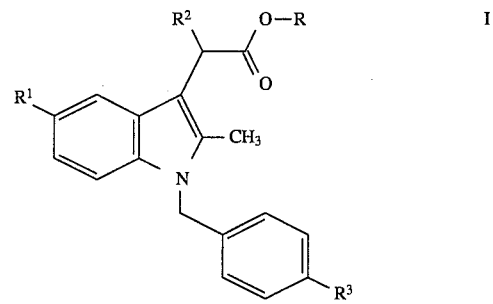

The invention also encompasses certain pharmaceutical compositions for treatment of inflammation and, in particular, cyclooxygenase-2 mediated diseases comprising compounds of Formula I.

DETAILED DESCRIPTION OF THE INVENTION

The invention encompasses the novel compound of Formula I as well as a method of treating cyclooxygenase-2 mediated diseases comprising administration to a patient in need of such treatment of a non-toxic therapeutically effective amount of a compound of Formula I,

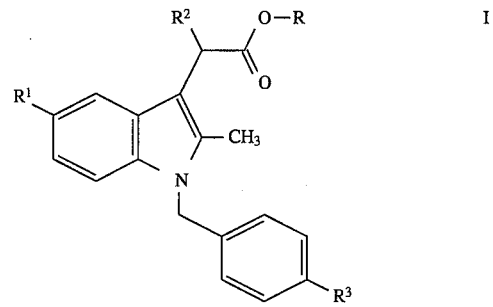

and pharmaceutically acceptable salts thereof wherein:

R is H, methyl, ethyl or propyl;

$R^1$ is halo or methyl;

$R^2$ is —H, methyl or ethyl;

$R^3$ is Br or I.

In one genus, the invention encompasses compounds of Formula I wherein

R is H or methyl;

$R^1$ is halo selected from Br, Cl and I, $R^2$ is H or methyl;

$R^3$ is Br.

Within this genus there is a class of compounds of Formula I wherein

R is H;

$R^1$ is Br;

$R^2$ is H or methyl;

$R^3$ is Br.

Illustrating the invention are the compounds of Formula I selected from (a) 2-(5-Bromo-1-(4-bromobenzyl)-2-methyl-1H-indol-3yl)propionic acid, sodium salt;

(b) (S)-(+)-2-(5-Bromo-1-(4-bromobenzyl)-2-methyl-1H-indol-3-yl)propionic acid, sodium salt;

(c) (R)-(−)-2-(5-Bromo- 1-(4-bromobenzyl)-2-methyl-1H-indol-3yl)-propionic acid, sodium salt; and (d) 2-(5-Bromo-1-(4-iodobenzyl)-2-methyl-1H-indol-3-yl)propionic acid, sodium salt.

Halogen includes F, Cl Br, and I.

Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzyl-ethylenediamine, diethylamine, 2-diethylaminoethanol, 2-dimethyl-aminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that in the discussion of methods of treatment which follows, references to the compounds of Formula I are meant to also include the pharmaceutically acceptable salts.

The Compound of Formula I is useful for the relief of pain, fever and inflammation of a variety of conditions including rheumatic fever, symptoms associated with influenza or other viral infections, common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, injuries, following surgical and dental procedures. In addition, such a compound may inhibit cellular neoplastic transformations and metastic tumor growth and hence can be used in the treatment of cancer. Compound I may also be of use in the treatment and/or prevention of cyclooxygenase-mediated proliferative disorders such as may occur in diabetic retinopathy and tumor angiogenesis.

Compound I will also inhibit prostanoid-induced smooth muscle contraction by preventing the synthesis of contractile prostanoids and hence may be of use in the treatment of dysmenorrhea, premature labor, asthma and eosinophil related disorders. It will also be of use in the treatment of Alzheimer's disease and osteoporosis.

By virtue of its high cyclooxygenase-2 (COX-2) activity and/or its specificity for cyclooxygenase-2 over cyclooxygenase-1 (COX-1 ), Compound I will prove useful as an alternative to conventional non-steroidal antiinflammatory drugs (NSAID'S) particularly where such non-steroidal antiinflammatory drugs may be contra-indicated such as in patients with peptic ulcers, gastritis, regional enteritis, ulcerative colitis, diverticulitis or with a recurrent history of gastrointestinal lesions; GI bleeding, coagulation disorders including anemia such as hypoprothrombinemia, haemophilia or other bleeding problems; kidney disease; those prior to surgery or taking anticoagulants.

Similarly, Compound I, will be useful as a partial or complete substitute for conventional NSAID'S in preparations wherein they are presently co-administered with other agents or ingredients. Thus in further aspects, the invention encompasses pharmaceutical compositions for treating cyclooxygenase-2 mediated diseases as defined above comprising a non-toxic therapeutically effective amount of the compound of Formula I as defined above and one or more ingredients such as another pain reliever including acetominophen or phenacetin; a potentiator including caffeine; an H2-antagonist, aluminum or magnesium hydroxide, simethicone, a decongestant including phenylephrine, phenylpropanolamine, pseudophedrine, oxymetazoline, ephinephrine, naphazoline, xylometazoline, propylhexedrine, or levo-desoxyephedrine; an antiitussive including codeine, hydrocodone, caramiphen, carbetapentane, or dextramethorphan; a diuretic; a sedating or non-sedating antihistamine. In addition the invention encompasses a method of treating cyclooxygenase mediated diseases comprising: administration to a patient in need of such treatment a non-toxic therapeutically effect amount of the compound of Formula I, optionally co-administered with one or more of such ingredients as listed immediately above.

For the treatment of any of these cyclooxygenase mediated diseases Compound I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating cyclooxygenase-2 mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compound I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the Order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following method (See also Scheme 1).

An aryl hydrazine II may be benzylated by treatment with benzyl halide III in the presence of diisopropylethyl amine or triethyl amine to provide N-benzyl hydrazine IV. This hydrazine may be reacted with ketone V to provide indole VI by first treating with acetic acid in toluene followed by treating the resulting hydrazone in solvent such as dioxane or ethanol containing a strong acid such as HCl or $H_2SO_4$. Alternatively, hydrazine II may be coupled first with ketone V under similar conditions to give indole VII which is then benzylated with III using sodium hydride in DMF or KHMDS in THF/DMPU to provide indole VI. Indole VI may then be treated with LiHMDS in THF or KHMDS in THF/DMPU followed by addition of a methyl or ethyl halide to provide Compound VIII. Hydrolysis of Compound VI or VIII with NaOH in methanol/THF gives Compound I. Compound I ($R^2$=H) can also be obtained without a hydrolytic step by using the acid form of V (R=H) in the Fischer indole reaction.

As appreciated by one skilled in the art, Compound I may be resolved into its corresponding enantiomers via chiral resolution or the individual isomers may be prepared from a chiral starting material.

Table I illustrates compounds of Formula Ia, which are representative of the present invention.

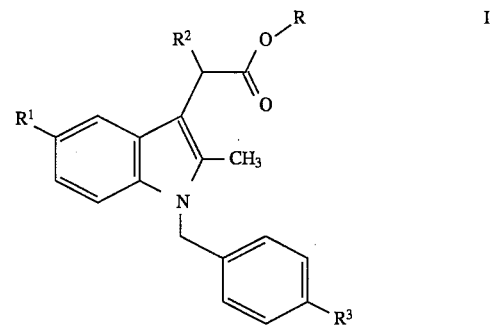

TABLE I

| Example No. | Stereo | R | $R^1$ | $R^2$ | $R^3$ |
| --- | --- | --- | --- | --- | --- |
| 1 | rac. | H | Br | $CH_3$ | Br |
| 2 | S (+) | H | Br | $CH_3$ | Br |
| 3 | R (−) | H | Br | $CH_3$ | Br |
| 4 | rac. | H | Br | $CH_3$ | I |
| 5 | | H | Cl | $CH_3$ | Br |
| 6 | | H | F | $CH_3$ | Br |
| 7 | | H | I | $CH_2CH_3$ | Br |

SCHEME 1

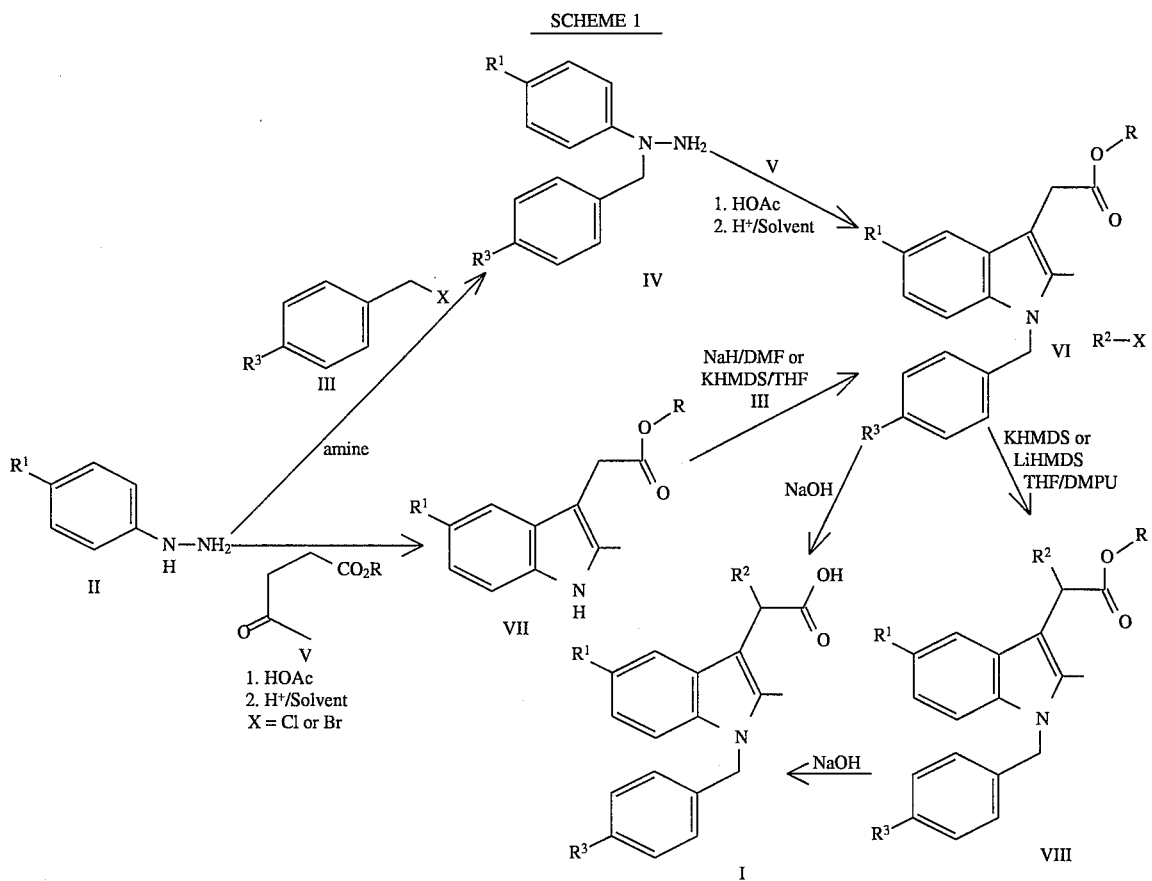

TABLE I-continued

| Example No. | Stereo | R | R¹ | R² | R³ |
| --- | --- | --- | --- | --- | --- |
| 8 | | CH₃ | Me | CH₃ | Br |

Assays for Determining Biological Activity

The compound of Formula I can be tested using the following assays to determine their cyclooxygenase-2 inhibiting activity.

Inhibition of Cyclooxygenase Activity

Compounds were tested as inhibitors of cyclooxygenase activity in whole cell cyclooxygenase assays. Both of these assays measured prostaglandin $E_2$ synthesis in response to arachidonic acid, using a radioimmunoassay. Cells used for these assays were human osteosarcoma 143 cells (which specifically express cyclooxygenase-2) and human U-937 cells (which specifically express cyclooxygenase-1 ). In these assays, 100% activity is defined as the difference between prostaglandin $E_2$ synthesis in the absence and presence of arachidonate.

Assay

For cyclooxygenase assays, osteosarcoma cells are cultured in 1 mL of media in 24-well multidishes (Nunclon) until confluent (1–2×10⁵ cells/well). U-937 cells are grown in spinner flasks and resuspended to a final density of 1.5×10⁶ cells/mL in 24-well multidishes (Nunclon). Following washing and resuspension of osteosarcoma and U-937 cells in 1 mL of Hanks balanced salts solution (HBSS), 2 µL of a DMSO solution of test compound or DMSO vehicle is added, and samples gently mixed. All assays are performed in triplicate. Samples and then incubated for 5 or 15 minutes at 37° C., prior to the addition of arachidonic acid. Arachidonic acid (peroxide-free, Cayman Chemical) is prepared as a 10mM stock solution in ethanol and further diluted 10-fold in HBSS. An aliquot of 10 µL of this diluted solution is added to the cells to give a final arachidonic acid concentration of 10 µM. Control samples are incubated with ethanol vehicle instead of arachidonic acid. Samples are again gently mixed and incubated for a further 10 min. at 37° C. For osteosarcoma cells, reactions are then stopped by the addition of 100 µL of 1 N HCl with mixing and by the rapid removal of the solution from cell monolayers. For U-937 cells, reactions are stopped by the addition of 100 µL of 1N HCl, with mixing. Samples are then neutralized by the addition of 100 µL of 1N NaOH and $PGE_2$ levels measured by radioimmunoassay.

Rat Paw Edema Assay—Protocol

Male Sprague-Dawley rats (150–200 g) were fasted overnight and were given po either vehicle (1% methocel or 5% Tween 80) or a test compound. One hour later, a line was drawn using a permanent marker at the level above the ankle in one hind paw to define the area of the paw to be monitored. The paw volume ($V_O$) was measured using a plethysmometer (Ugo-B asile, Italy) based on the principle of water displacement. The animals were then injected subplantarly with 50 µl of 1% carrageenan solution in saline (FMC Corp, Maine) into the paw using an insulin syringe with a 25-gauge needle (i.e. 500 µg carrageenan per paw). Three hours later, the paw is volume ($V_3$) was measured and the increases in paw volume ($V_3-V_O$) were calculated. The animals were sacrificed by $CO_2$ aphyxiation and the absence or presence of stomach lesions scored. Data were compared with the vehicle-control values and percent inhibition calculated. Since a maximum of 60–70% inhibition (paw edema) was obtained with standard NSAIDs, $ED_{30}$ values were used for comparison. All treatment groups were coded to eliminate observer bias.

NSAID-Induced Gastropathy in Rats Rationale

The major side effect of conventional NSAID's is their ability to produce gastric lesions in man. This action is believed to be caused by inhibition of COX-1 in the gastrointestinal tract. Rats are particularly sensitive to the actions of NSAID's. In fact, rat models have been used commonly in the past to evaluate the gastrointestinal side effects of current conventional NSAID's. In the present assay, NSAID-induced gastrointestinal damage is observed by measuring fecal 51Cr excretion after systemic injection of 51Cr-labeled red blood cells. Fecal 51Cr excretion is a well-established and sensitive technique to detect gastrointestinal integrity in animals and man.

Methods

Male Sprague Dawley rats (150–200 g) are administered orally a test compound either once (acute dosing) or b.i.d. for 5 days (chronic dosing). Immediately after the administration of the last dose, the rats are injected via a tail vein with 0.5 mL of $^{51}$Cr-labeled red blood cells from a donor rat. The animals are placed individually in metabolism cages with food and water ad lib. Feces are collected for a 48 h period and $^{51}$Cr fecal excretion is calculated as a percent of total injected dose. $^{51}$Cr-labeled red blood cells are prepared using the following procedures. Ten mL of blood is collected in heparinized tubes via the vena cava from a donor rat. Plasma is removed by centrifugation and replenished with equal volume of Hanks' balanced salt solution (HBSS). The red blood cells are incubated with 400 µCi of sodium 51 chromate for 30 min. at 37° C. At the end of the incubation, the red blood cells are washed twice with 20 mL HBSS to remove free sodium $^{51}$ chromate. The red blood cells are finally reconstituted in 10 mL HBSS and 0.5 mL of the solution (about 20 µCI) is injected per rat.

Protein-Losing Gastropathy in Squirrel Monkeys Rationale

Protein-losing gastropathy (manifested as appearance of circulating cells and plasma proteins in the GI tract) is a significant and dose-limiting adverse response to standard non-steroidal anti-inflammatory drugs (NSAID's). This can be quantitatively assessed by intravenous administration of $^{51}CrCl_3$ solution. This isotopic ion can avidly bind to cell and serum globins and cell endoplasmic reticulum. Measurement of radioactivity appearing in feces collected for 24 h after administration of the isotope thus provides a sensitive and quantitative index of protein-losing gastropathy.

Methods

Groups of male squirrel monkeys (0.8 to 1.4 kg) are treated by gavage with either 1% methocell or 5% Tween 80 in H2O vehicles, 3mL/kg b.i.d.) or test compounds at doses from 1–100 mg/kg b.i.d. for 5 days. Intravenous $^{51}$Cr (5µCi/kg in 1 ml/kg phosphate buffer saline (PBS)) is administered 1 h after the last drug/vehicle dose, and feces collected for 24 h in a metabolism cage and assessed for excreted $^{51}$Cr by gamma-counting. Venous blood is sampled 1 h and 8 h after the last drug dose, and plasma concentrations of drug measured by RP-HPLC.

Compounds of the present invention are inhibitors of cyclooxygenase-2 and are thereby useful in the treatment of cyclooxygenase-2 mediated diseases as enumerated above. The activities of the compounds against cyclooxygenase may be seen in the representative results shown below. In the assay, inhibition is determined by measuring the amount of prostaglandin $E_2$ ($PGE_2$) synthesized in the presence of arachidonic acid, cyclooxygenase-1 or cyclooxygenase-2 and a putative inhibitor. The $IC_{50}$ values represent the concentration of putative inhibitor required to return $PGE_2$ synthesis to 50% of that obtained as compared to the uninhibited control.

The results for inhibition of $PGE_2$ production may be seen in Table II.

The Table also contains data for the compound α-(1-p-chlorobenzyl-2 -methyl-5-methoxy-3-indolyl)propionic acid (also known as MK-555). This compound is disclosed in British Patent Specification 957,990 (May 13, 1964) as having anti-inflammatory activity. As can be seen from the data, the compounds of the present invention are generally more potent than MK-555, especially in vivo.

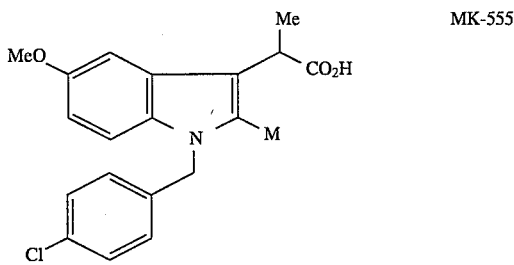

MK-555

TABLE II

| Example No. | COX-2 ($IC_{50}$) | COX-1 ($IC_{50}$) | Rat paw edema ($ED_{30}$) |
| --- | --- | --- | --- |
| 1 | 1.9 nM | 10 uM | 0.26 |
| 2 | 13 nM | 1.1 uM | 0.28 |
| 3 | 1 nM | 32 uM | 0.57 |
| MK-555 | 10 nM | 10 μM | 3.0 |

The invention will now be illustrated by the following non-limiting examples in which, unless stated otherwise:

(i) all operations were carried out at room or ambient temperature, that is, at a temperature in the range 18°–25° C., (ii) evaporation of solvent was carried out using a rotary evaporator under reduced pressure (600–4000 pascals: 4.5–30 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

The following abbreviations have the indicated meanings:
Ac=acetyl
DMF=N,N-dimethylformamide
DMPU=1,3-dimethyl-3,4,5,6-tetrahydro-2(1H)-1H-pyrimidinone
$Et_3N$=triethylamine
KHMDS=potassium hexamethyldisilazane
LDA=lithium diisopropylamide
LiHMDS=lithium hexamethyldisilazane
NSAID=non-steroidal anti-inflammatory drug
r.t.=room temperature
rac.=racemic
THF=tetrahydrofuran
Alkyl group abbreviations
Me=methyl
Et=ethyl
Bu=butyl

EXAMPLE 1

2-(5-Bromo-1-(4-bromobenzyl)-2-methyl-1H-indol-3-yl)propionic acid, sodium salt

Step 1: N-(4-Bromobenzyl)-N-(4-bromophenyl)hydrazine

4-Bromophenylhydrazine hydrochloride (30 g, 134 mmol), p-bromobenzyl bromide (40 g, 161 mmol), diisopropylethylamine (43 g, 335 mmol) and tetrabutylammonium bromide (13 g, 40 mmol) were stirred together in 400 mL of $CH_2Cl_2$ at r.t. overnight. The mixture was then washed with $H_2O$, dried over $MgSO_4$ and the title product was purified by flash chromatography on silica using EtOAc:hexane (30:70) and by a swish in hexanes. Yield 34 g (71%).

$^1$H NMR ($CDCl_3$) 4.50 (2H, s), 6.93 (2H, d), 7.13 (2H, d), 7.32 (2H, d), 7.45 (2H, d).

Step. 2: Ethyl 2-(5-bromo-1-(4-bromobenzyl)-2-methyl-1H-indol-3-yl)acetate

At 0° C., acetic acid (14 mL, 2.2 equiv.) was added slowly to a solution of the hydrazine of Step 1 (39 g, 110 mmol) and ethyl levulinate (19 g, 1.2 equiv.) in 400 mL toluene and the mixture was aged at 0° C. for 30 min. $Na_2SO_4$ was then added and the mixture was stirred at 40° C. for 15 min. The solution was filtered and concentrated under vacuum to yield the hydrazone. To this hydrazone, a solution of HCl in EtOH (prepared from 53 mL of acetyl chloride and 300 mL EtOH at 0° C.) was added and the mixture was heated to reflux for 5 h. It was then cooled to 0° C. and the precipitate was filtered and washed with cold isopropanol. The solid was taken up in 500 mL of boiling EtOAc and filtered. Concentration of the filtrate afforded 42.9 g (84% yield) of the title compound. $^1$H NMR ($CDCl_3$) 1.25 (3H, t), 2.31 (3H, s), 3.67 (2H, s), 4.15 (2H, q), 5.23 (2H, s), 6.79 (2H, d), 7.03 (1H, d), 7.20 (1H, dd), 7.38 (2H, d), 7.72 (1H, d).

Step 3: Ethyl 2-(5-bromo-1-(4-bromobenzyl)-2-methyl-1H-indol-3-yl)propionate

At –78° C., a solution of KHMDS 0.56 in toluene (50 mL, 1.0 equiv.) was added slowly to a solution of the product of Step 2 (12.67 g, 27.2 mmol) in 132 mL of THF:DMPU 10:1 and the mixture was aged at –78° C. for 35 min. MeI (2.0 mL, 1.2 equiv.) was then added and the reaction mixture was warmed to 0° C. over 45 min. A saturated solution of $NH_4Cl$ was then added and the product was extracted with EtOAc, the extracts were dried over $Na_2SO_4$, and the product purified by flash chromatography on silica with EtOAc:toluene:hexane 1.5:50:50 to yield the title compound, 11.84 g (89%). $^1$H NMR (CDCl$_3$) 1.20 (3H, t), 1.58 (3H, d), 2.30 (3H, s), 3.93 (1H, q), 4.14 (2H, m), 5.21 (2H, s), 6.77 (2H, d), 7.02 (1H, d), 7.18 (1H, dd), 7.38 (2H, d), 7.82 (1H, d).

Step 4: 2-(5-Bromo-1-(4-bromobenzyl)-2-methyl-1H-indol-3-yl)propionic acid

A mixture of the product of Step 3 (11.59 g, 24.2 mmol), THF (125 mL), MeOH (60 mL), H$_2$O (30 mL) and 10 N NaOH (10 mL) was stirred at r.t. overnight. The mixture was then acidified with 2N HCl and the product was extracted in EtOAc, the extracts were dried over Na$_2$SO$_4$, and the product was purified by flash chromatography on silica with EtOAc:toluene:AcOH 5:95: 1. It was then swished in ether:hexane 1:2 to yield 10.29 g, 94%, of the title product. $^1$H NMR (CD$_3$COCD$_3$) 1.50 (3H, d), 2.38 (3H, s), 4.05 (1H, q), 5.44 (2H, s), 6.95 (2H, d), 7.16 (1H, dd), 9.28 (1H, d), 7.47 (2H, d), 7.80 (1H d).

Analysis calculated for C$_{19}$H$_{17}$Br$_2$NO$_2$ C, 50.58; H, 3.80; N, 3.10 Found: C, 50.25; H, 3.69; N, 3.07

Step 5: 2-(5-Bromo-1-(4-bromobenzyl)-2-methyl-1H-indol-3-yl)propionic acid, sodium salt To the acid of Step 4 in EtOH was added 1 eq. of NaOH and the resulting solution was evaporated to dryness. Lyophilization of the resulting residue yielded the title compound.

EXAMPLE 2

(S)-(+)-2-(5-Bromo-1-(4-bromophenyl)-2-methyl-1H-indol-3yl)propionic acid, sodium salt Step 1: 2-(5-Bromo-1-(4-bromobenzyl)-2-methyl- 1H-indol-3-yl)acetyl acid The product of Example 1, Step 2, was hydrolyzed to the title product using the procedure of Example 1, Step 4. Yield 98%.

Step 2: 3-(2-(5-Bromo-1-(4-bromobenzyl)-2-methyl-1H-indol-3-yl)acetyl)-4(S)-methyl-5(R)-phenyl-2-oxazolidinone At 0° C., oxalyl chloride (12 mL, 1.5 equiv.) was slowly added to a solution of the acid of Step 1 (39.5 g, 90.3 mmol) and DMF (700 L) in 700 mL of THF/CH$_2$Cl$_2$ (1:1) and the mixture was aged at 0° C. for 30 min. and at r.t. for 1 h. The solvents were evaporated and the acid chloride was stripped once with toluene.

At −78° C., 1.6M BuLi in hexane (65 mL, 104 mmol) was added dropwise to a solution of (4S)(5R)-4-methyl-5-phenyl-2-oxazolidinone (17.97 g, 104 mmol) in 170 mL of THF and the mixture was stirred at −78° C. for 10 min. Then, a solution of the acid chloride in 300 mL of THF was added and the mixture was aged at 0° C. for 15 min. A saturated solution of NH$_4$Cl (500 mL), HOAc (10 mL) and water (300 mL) was then added. The product was extracted with EtOAc and the extracts dried over Na$_2$SO$_4$. The crude solution was filtered through a small pad of silica, concentrated to dryness and stripped with toluene. The solid was swished in ether:hexane (1:1) overnight, filtered and washed with the same solvent to yield 49.65 g (92%) of the title compound. $^1$H NMR (CDCl$_3$) 0.93 (3H, d) 2.32 (3H, s) 4.39 (2H, s), 4.79 (1H, m), 5.24 (2H, s), 5.71 (1H, d), 6.80 (2H, d), 7.03 (1H, d), 7.20 (1H, dd), 7.30 (2H, dd), 7.33–7.47 (5H, m), 7.68 (1H, d).

Step 3: 3-(2-(S)-(5-Bromo-1-(4-bromobenzyl)-2-methyl-1H-indol-3-yl)propanoyl-4 (S)-methyl-5(R)-phenyl-2-oxazolidinone Using the procedure of Example 1, Step 3 but without DMPU as solvent, the methylation of the product of Step 2 (12.13 g, 20.3 mmol) afforded a mixture of 2 diastereomers. They were separated by flash chromatography on silica with EtOAc:toluene:hexane 1.5:50:50 to 5:50:50. The title compound, the major isomer, was eluted first. It was then recrystallized from 200 mL EtOAc:hexane (1:3) at 0° C. to give 7.75 g (62%), of pure material.

$^1$H NMR (CDCl$_3$) 0.96 (3H, d), 1.54 (3H, d), 2.38 (3H, s), 4.68 (1H, m), 5.14 (1H, q), 5.20 (2H, AB system), 5.34 (1H, d), 6.77 (2H, d), 7.00 (2H, d), 7.17 (1H, d), 7.23 (2H, d), 7.35 (5H, m), 7.85 (1H, s).

Step 4: (S)-(+)-2-(5-Bromo-1-(4-bromophenyl)-2-methyl-1H-indol-3-yl)propionic acid The product of Step 3 (29.72 g, 48.7 mmol) was dissolved in 500 mL of hot THF. The solution was cooled to 5° C., 170 mL of ice water was added, followed by a slow addition of 30% H$_2$O$_2$ (22 mL) and 1.0 N LiOH (100 mL). Ice was added occasionally during the addition of LiOH to keep the temperature below 4° C. The mixture was then aged at 0°–4° C. for 1 hour and was then allowed to warm to 8° C. It was cooled again below 5° C. by addition of ice, and a solution of Na$_2$SO$_3$ 1.5M (140 mL) was added slowly. Ice was still added occasionally during the reduction of H$_2$O$_2$ to keep the temperature below 5° C. The mixture was aged at 0° C. for 30 min. and then acidified with 2 N HCl. The product was extracted with EtOAc, dried over Na$_2$SO$_4$ and purified by flash chromatography on silica with EtOAc:toluene:AcOH 2.5:97.5:1 and 5:95:1. The solid was swished in 600 mL ether:hexane 1:3 to yield 20.97 g (95%) of pure material. $^1$H NMR identical to Example 1. $[\alpha]_D^{25}$=+38.3° (c=0.7, EtOH).

Step 5: (S)-(+)-2-(5-Bromo-1-(4-bromophenyl)-2-methyl-1-indol-3yl)propionic acid, sodium salt Using the acid from Step 4 and the procedure of Example 1 Step 5, the title compound was obtained.

EXAMPLE 3

(R)-(−)-2-(5-Bromo-1-(4-bromobenzyl)-2-methyl-1H-indol-3-yl)propionic acid, sodium salt Using the procedure of Example 2, but substituting the oxazolidinone of Step 2 by its enantiomer, the title compound was obtained. $[\alpha]D^{25}$=−38.7 (c=1, EtOH).

EXAMPLE 4

2-(5-Bromo-1-(4-iodobenzyl)-2-methyl-1H-indolo-3-yl)propionic acid, sodium salt.

Step 1:
Ethyl 2-(5-bromo-2-methyl-1H-indol-3-yl)acetate

A mixture of 4-bromophenylhydrazine hydrochloride (2.23 g, 10 mmol) and ethyl levulinate (1.58 g, 11 mmol) in 10 mL HOAc was heated to reflux for 20 h. The HOAc was removed under vaccum. The residue was dissolved in 10 mL EtOH. A solution of HCl in dioxane (12 mmol, 4M solution) was added. The mixture was heated to reflux for 4 h. The mixture was concentrated under vacuum and the residue was purified by flash chromatography on silica gel, eluting with 20% EtOAc in hexane to afford 2.1 g (78%) of the title compound.

$^1$H NMR (CD$_3$COCD$_3$) 1.20 (3H, t, J=7.1 Hz), 2.41 (3H, s), 3.66 (2H, s), 4.08 (2H, q, J=7.1 Hz), 7.14 (1H, d, J=1.9 Hz), 7.24 (1H, d, J=1.8 Hz).

Step 2: Ethyl 2-(5-bromo-1-(4-iodobenzyl)-2-methyl-1H-indol-3 -yl)acetate

To a solution of the product of Step 1 (536.2 mg, 2 mmol) and 4-iodobenzyl chloride (504 mg, 2 mmol) in dry DMF (10 mL) at 0° C. was added sodium hydride (80 mg, 2 mmol, 60% in oil). The mixture was stirred at 20° C. for 20 hours and a saturated NH$_4$Cl solution (10 mL) was added. The mixture was extracted with EtOAc, the extracts were dried over MgSO$_4$ and concentrated to an oil. The oil was purified by flash chromatography on silica gel, eluting with 20% EtOAc in hexane to afford 704 mg (69%) of the title compound. $^1$H NMR (CDCl$_3$) 1.23 (3H, t, J=7.1 Hz), 2.28 (3H, s), 3.65 (2H, s), 4.12 (2H, q, J=7.1 Hz), 5.19 (2H, s), 6.64 (2H, d, J=8.3 Hz), 6.98 (1H, d, J=8.6 Hz), 7.17 (1H, dd, J=8.6 Hz, 1.8 Hz), 7.56 (2H, d, J=8.3 Hz), 7.68 (1H, d, 1.8 Hz).

Step 3: Ethyl 2-(5-bromo-1-(4-iodobenzyl)-2-methyl-1H-indol-3y;)propionate

A solution of the product of Step 2 (483 mg, 0.94 mmol) in THF (1 mL) was added to a cold (–78° C.) solution of LiHMDS (1.03 mmol, 1M) in THF (4 mL). The mixture was warmed to –50° C. briefly and then cooled to –78° C. MeI (284 mg, 2 mmol) was added. The mixture was warmed to –10° C. for 1 h. Saturated NH4Cl solution (10 mL) was added. The mixture was extracted with EtOAc, the extracts were dried over MgSO$_4$ and concentrated to an oil. The oil was purified by flash chromatography on silica gel, eluting with 20% EtOAc in hexane to afford 526 mg (70%) of the title compound.

$^1$H NMR (CDCl$_3$) 1.17 (3H, t, J=7.2 Hz), 1.56 (3H, d, J=7.3 Hz), 2.28 (3H, s), 3.90 (1H, q, J=7.3 Hz), 4.12 (2H, m), 5.18 (2H, s), 6.62 (2H, d, J=8.3 Hz), 6.98 (1H, d, J=8.6 Hz), 7.15 (1H, dd, J=8.6 Hz, 1.8 Hz), 7.56 (2H, d, J=8.3 Hz), 7.79 (1H, d, J=1.8 Hz).

Step 4: 2-(5-Bromo-1-(4-iodobenzyl)-2-methyl-1H-indol-3-yl)propionic acid

A mixture of the product of Step 3 (369 mg, 0.7 mmol), NaOH (0.7 mL, 3 N), THF (2 mL) and MeOH (3 mL) was stirred at 20° C. for 4 h. The mixture was acidifed with 1 N HCl and extracted with EtOAc. The extracts were dried over MgSO$_4$ and concentrated to a solid which was swished in ether:hexane (1:10) to give 268 mg (75%) of the title compound.

Step 5: 2-(5-Bromo-1-(4-iodobenzyl)-2-methyl-1H-indol-3-yl)propionic acid, sodium salt Using the acid from Step 4 and the procedure of Example 1 Step 5, the title compound was obtained.

$^1$H NMR (CD$_3$SOCD$_3$) 1.27 (3H, d, J=7.2 Hz), 2.26 (3H, s), 3.44 (1H, q, J=7.3 Hz), 5.29 (2H, s), 6.75 (2H, d, J=8.3 Hz), 7.02 (1H, dd, J=8.6 Hz, 1.9 Hz), 7.21 (1H, d, J=8.6 Hz), 7.63 (2H, d, J=8.3 Hz), 7.94 (1H, d, J=1.9 Hz).

What is claimed is:

1. A compound of structural Formula I:

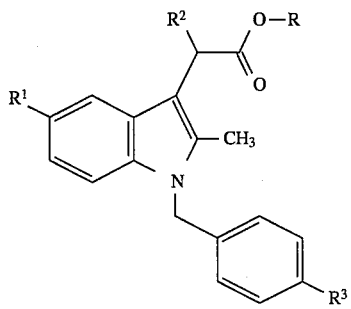

or a pharmaceutically acceptable salt thereof, wherein:

R is H, methyl, ethyl or propyl;

R$^1$ is halo or methyl;

R$^2$ is —H, methyl or ethyl;

R$^3$ is Br.

2. A compound of claim 1 wherein

R is H or methyl;

R$^1$ is halo selected from Br, Cl and I,

R$^2$ is H or methyl;

R$^3$ is Br.

3. A compound of claim 2 wherein

R is H;

R$^1$ is Br;

R$^2$ is H or methyl;

R$^3$ is Br.

4. A compound according to claim 3 selected from the group consisting of (a) 2-(5-Bromo-1-(4-bromobenzyl)-2-methyl-1H-indol-3-yl)propionic acid, sodium salt;

(b) (S)-(+)-2-(5-Bromo-1-(4-bromobenzyl)-2-methyl-1H-indol-3-yl)propionic acid, sodium salt;

(c) (R)-(−)-2-(5-Bromo-1-(4-bromobenzyl)-2-methyl-1H-indol-3-yl)-propionic acid, sodium salt; and (d) 2-(5-Bromo-1-(4-iodobenzyl)-2-methyl-1H-indol-3-yl)propionic acid, sodium salt.

5. A compound which is (S)-(+)-2-(5-Bromo-1-(4-bromobenzyl)-2-methyl- 1H-indol-3-yl)propionic acid, sodium salt.

6. A pharmaceutical composition for treating an inflammatory disease susceptable to treatment with an non-steroidal anti-inflammatory agent comprising: a non-toxic therapeutically effective amount of a compound according to claim 1 and a pharmaceutically acceptable carrier.

7. A pharmaceutical composition for treating inflammation comprising:

a non-toxic therapeutically effective amount of a compound according to claim 1 and a pharmaceutically acceptable carrier.

8. A method of treating an inflammatory disease susceptable to treatment with an non-steroidal anti-inflammatory agent comprising:

administration to a patient in need of such treatment of a non-toxic therapeutically effective amount of a compound according to claim 1 and a pharmaceutically acceptable carrier.

9. A compound of claim 1 wherein

R is H or methyl;

R$^1$ is Br of Cl or methyl;

R$^2$ H or methyl;

R$^3$ is Br.

* * * * *